United States Patent
Feller et al.

(10) Patent No.: US 8,163,006 B2
(45) Date of Patent: Apr. 24, 2012

(54) REDUCED PROFILE AAA DEVICE

(75) Inventors: Frederick Feller, Coral Springs, FL (US); David C. Majercak, Stewartsville, NJ (US); Jin S. Park, Parsippany, NJ (US)

(73) Assignee: Cordis Corporation

( * ) Notice: Subject to any disclaimer, the term of this patent is extended or adjusted under 35 U.S.C. 154(b) by 678 days.

(21) Appl. No.: 11/190,367

(22) Filed: Jul. 27, 2005

(65) Prior Publication Data
US 2006/0025850 A1    Feb. 2, 2006

Related U.S. Application Data

(60) Provisional application No. 60/591,953, filed on Jul. 28, 2004.

(51) Int. Cl.
*A61F 2/82* (2006.01)
(52) U.S. Cl. .............. 623/1.35; 623/1.13; 623/1.16
(58) Field of Classification Search ............ 623/1.35, 623/1.15, 1.16; A61F 2/06
See application file for complete search history.

(56) References Cited

U.S. PATENT DOCUMENTS

| | | | |
|---|---|---|---|
| 5,662,675 A | 9/1997 | Polanskyj et al. | |
| 6,520,988 B1 * | 2/2003 | Colombo et al. | 623/1.35 |
| 6,884,260 B2 | 4/2005 | Kugler et al. | |
| 7,175,657 B2 * | 2/2007 | Khan et al. | 623/1.35 |
| 2001/0039449 A1 * | 11/2001 | Johnson et al. | 623/1.19 |
| 2001/0053930 A1 * | 12/2001 | Kugler et al. | 623/1.13 |
| 2003/0033003 A1 * | 2/2003 | Harrison et al. | 623/1.15 |
| 2003/0120263 A1 | 6/2003 | Ouriel et al. | |
| 2003/0149473 A1 | 8/2003 | Chouinard et al. | |
| 2005/0113906 A9 * | 5/2005 | Bolduc et al. | 623/1.35 |
| 2005/0273157 A1 * | 12/2005 | Pinchasik | 623/1.15 |

FOREIGN PATENT DOCUMENTS

| | | |
|---|---|---|
| EP | 1356786 A1 | 6/2003 |
| EP | 1386-590 B1 | 11/2010 |
| JP | 2003/515386 | 5/2003 |
| WO | WO 95-21592 A1 | 8/1995 |
| WO | WO 01-35864 A1 | 5/2001 |

OTHER PUBLICATIONS

Notification of Reasons for Refusal issued on corresponding Japanese Patent Application No. 2005-216912 dated Jul. 27, 2010.

* cited by examiner

*Primary Examiner* — Thomas J Sweet
*Assistant Examiner* — Jason-Dennis Stewart

(57) ABSTRACT

An abdominal aortic aneurysm endoprosthesis having a reduced profile for percutaneous delivery of the endoprosthesis. The endoprosthesis provides a cranial section supported by a stent, and a bifurcated caudal section having at least two legs each of which are supported by individual stents. The individual stents of each leg of the caudal section are staggered so as not to line up with one another. Altering the lengths of the legs permits nesting of the endoprosthesis. Optimizing the expansion ratio and radial strength of the endoprosthesis is achieved by altering the dimensions of the starting material from which the stent segments are fabricated, by altering the final austenite temperature of the starting materials, or by changing the structural configuration of the stent segments. A graft material is attached to at least a portion of the cranial section and to all of the caudal section of the endoprosthesis.

6 Claims, 1 Drawing Sheet

REDUCED PROFILE AAA DEVICE

CROSS REFERENCE TO RELATED APPLICATIONS

This application claims the benefit of U.S. Provisional Patent Application Ser. No. 60/591,953 filed Jul. 28, 2004.

BACKGROUND OF THE INVENTION

1. Field of the Invention

The present invention relates to abdominal aortic aneurysm devices, and more particularly, to a reduced profile abdominal aortic aneurysm device for percutaneous delivery.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be highly durable, extendable and re-configurable while maintaining acute and long-term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta.

SUMMARY OF THE INVENTION

The reduced profile abdominal aortic aneurysm repair device of the present invention overcomes the limitations associated with the percutaneous delivery of stent grafts as briefly described above.

In accordance with one aspect, the present invention is directed to an endoprosthesis. The endoprosthesis comprises an anchoring and sealing component having a cranial section comprising a stent having an expansion ratio of greater than about 7, a caudal section having at least two legs in fluid communication with the cranial section, each of the at least two legs comprising a plurality of individual stents, and graft material affixed to at least a portion of the cranial section and the at least two legs thereby forming at least two fluid flow conduits and at least two endolegs connectable to the at least two fluid flow conduits of the anchoring and sealing component.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
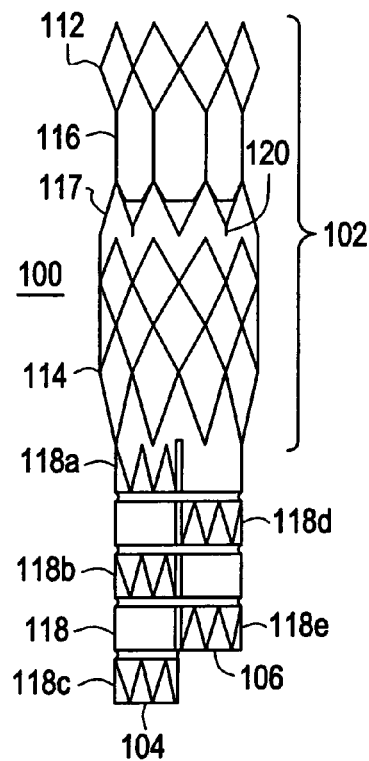
FIG. 1 is a diagrammatic representation of an exemplary supra-renal anchoring and sealing prosthesis in accordance with the present invention.

The present invention is directed to an endovascular graft which may be utilized as a component in a system for use in treating or repairing aneurysms. Systems for treating or repairing aneurysms such as abdominal aortic aneurysms and thoracic aortic aneurysms come in many forms. A typical system includes an anchoring and/or sealing component which is positioned in healthy tissue above the aneurysm and one or more grafts which are in fluid communication with the anchoring and/or sealing component and extend through the aneurysm and anchor in healthy tissue below the aneurysm. Essentially, the grafts are the components of the system that are utilized to establish a fluid flow path from one section of an artery to another section of the same or different artery, thereby bypassing the diseased portion of the artery. Current systems are preferably percutaneously delivered and deployed.

The stent segments of the present invention may be formed from any number of suitable biocompatible materials, including metals, polymers and ceramics. In a preferred embodiment, the stents are preferably self-expandable and formed from a shape memory alloy. Such an alloy may be deformed from an original, heat-stable configuration to a second, heat-unstable configuration. The application of a desired temperature causes the alloy to revert to an original heat-stable configuration. A particularly preferred shape memory alloy for this application is binary nickel titanium alloy comprising about 55.8 percent Ni by weight, commercially available under the trade designation NITINOL. This NiTi alloy undergoes a phase transformation at physiological temperatures. A stent made of this material is deformable when chilled. Thus, at low temperatures, for example, below twenty degrees centigrade, the stent is compressed so that it can be delivered to the desired location. The stent may be kept at low temperatures by circulating chilled saline solutions. The stent expands when the chilled saline is removed and it is exposed to higher temperatures within the patient's body, generally around thirty-seven degrees centigrade.

In preferred embodiments, each stent is fabricated from a single piece of alloy tubing. The tubing is laser cut, shape-set by placing the tubing on a mandrel, and heat-set to its desired expanded shape and size.

In preferred embodiments, the shape setting is performed in stages at five hundred degrees centigrade. That is, the stents are placed on sequentially larger mandrels and briefly heated to five hundred degrees centigrade. To minimize grain growth, the total time of exposure to a temperature of five hundred degrees centigrade is limited to five minutes. The stents are given their final shape set for four minutes at five hundred fifty degrees centigrade, and then aged to a temperature of four hundred seventy degrees centigrade to import the proper martensite to austenite transformation temperature, then blasted, as described in detail subsequently, before electropolishing. This heat treatment process provides for a stent that has a martensite to austenite transformation which occurs over a relatively narrow temperature range; for example, around fifteen degrees centigrade.

To improve the mechanical integrity of the stent, the rough edges left by the laser cutting are removed by combination of mechanical grit blasting and electropolishing. The grit blasting is performed to remove the brittle recast layer left by the laser cutting process. This layer is not readily removable by the electropolishing process, and if left intact, could lead to a brittle fracture of the stent struts. A solution of seventy percent methanol and thirty percent nitric acid at a temperature of minus forty degrees centigrade or less has been shown to work effectively as an electropolishing solution. Electrical parameters of the electropolishing are selected to remove approximately 0.00127 cm of material from the surfaces of the struts. The clean, electropolished surface is the final desired surface for attachment to the graft materials. This surface has been found to import good corrosion resistance, fatigue resistance, and wear resistance.

The graft material or component, may be made from any number of suitable biocompatible materials, including woven, knitted, sutured, extruded, or cast materials comprising polyester, polytetrafluoroethylene, silicones, urethanes, and ultralight weight polyethylene, such as that commercially available under the trade designation SPECTRA™. The materials may be porous or nonporous. Exemplary materials include a woven polyester fabric made from DACRON™ or other suitable PET-type polymers.

One of the challenges in abdominal aortic aneurysm repair devices is profile. More specifically, loading an abdominal aortic aneurysm repair device into a true percutaneous (13F) delivery device is a difficult task given the amount of material associated with the repair device. The anchor and sealing component of the repair device is the largest component. The anchoring and sealing component comprises a trunk section and a bifurcated section wherein the two legs thereof are supported by metallic stents. There are a number of design features that may be built into the anchoring and sealing component of the endovascular graft that may be utilized to reduce its profile, thereby making it a truly percutaneous device ((13F); namely, leaving spaces between the stent components in each of the legs and staggering the position of the stent components in each of the legs such that no two stent components line up. In this manner, the two legs of the bifurcated section may be nested during deployment, thereby reducing profile. It is important to note, however, that by staggering the stent components of the bifurcated section, the column strength of each leg may be somewhat comprised due to spacing between the stent components which in turn may lead to a cannulation problem during deployment. This problem may be overcome by connecting the two legs together to improve column strength during deployment. In addition, the tube from which the stent is cut may be modified to optimize the expansion range as well as the radial strength by changing the geometry of the device as is explained in detail subsequently.

Referring now to FIG. 1, there is illustrated an exemplary embodiment of an anchoring and sealing component 100 in accordance with the present invention. As illustrated, the anchoring and sealing component 100 comprises a trunk section 102 and a bifurcated section, including two legs 104, 106. Graft material, not illustrated, is affixed to at least a portion of the trunk section 102 and all of the legs 104, 106. The graft material is attached to various portions of the underlying structure by sutures, not shown. As illustrated, the graft material is affixed with a continuous stitch pattern on the end of the trunk section 102 and by single stitches elsewhere. It is important to note that any pattern may be utilized and other devices, such as staples, may be utilized to connect the graft material, not shown, to the underlying structure. The sutures, not illustrated, may comprise any suitable biocompatible material that is preferably highly durable and wear resistant.

Figure 2:
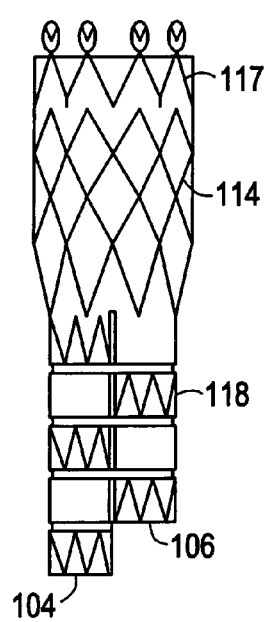
FIG. 2 is a diagrammatic representation of an exemplary infra-renal anchoring and sealing prosthesis in accordance with the present invention.

The underlying structure of the trunk section 102 comprises a substantially tubular stent structure or lattice comprising multiple stent sections. The stent or lattice structure comprises a single row of diamond elements 112 on one end, multiple rows of diamond elements 114 on the other end, a plurality of longitudinal struts 116 and a single, substantially zigzag shaped stent element 117. The plurality of longitudinal struts 116 are connected to the apexes of the diamond elements 114. The single, substantially zigzag shaped stent element 117 comprises a number of barbs 120 for anchoring the device in the vessels This exemplary embodiment may be utilized for anchoring and sealing in positions wherein there are branches off the main artery. For example, this exemplary embodiment may be utilized for supra-renal anchoring. Accordingly, the graft material is only attached below the longitudinal struts 116 so that blood may flow into the renal arteries from the aorta. An infra-renal design is illustrated in FIG. 2. In this exemplary embodiment, no longitudinal struts are required to cross branch arteries.

The underlying structure of the bifurcated section comprises a plurality of individual, substantially tubular stent elements 118. Each stent element 118 comprises a substantially zigzag pattern. As illustrated, leg 104 comprises three stent elements 118a, 118b, 118c and leg 106 comprises two stent elements 118d, 118e. Also illustrated is the fact that the stent elements do not line up and the legs are of two different lengths. As stated above, this design allows for nesting of the legs 104, 106 such that the profile of the overall device is reduced.

A percutaneous device utilized to treat a vessel larger than about twenty-eight mm has to go through a large expansion range, for example, an expansion ratio of greater than seven, wherein the expansion ratio equals the expansion diameter divided by the crimp diameter. Therefore, the amount of strain exerted on the stent or lattice structure is unacceptable for conventional Nitinol stent structures and the radial strength is also somewhat compromised. Accordingly, the stent or lattice structure of the trunk portion 102 of the anchoring and sealing component 100 may be modified to optimize the expansion range as well as the radial strength by changing the number of apexes or diamonds 114 comprising the structure, changing the dimension of the starting tube dimension and changing the final austenite temperature or $A_F$.

Figure 3:
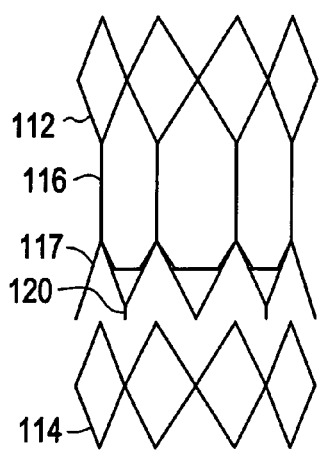
FIG. 3 is a diagrammatic representation of a trunk portion of the supra-renal anchoring and sealing prosthesis of FIG. 1.

In the exemplary embodiment the lattice comprising the trunk portion 102 is cut from a Nitinol tube that has an inside diameter of about 0.058 inches and an outside diameter of about 0.086 inches. Once the lattice is cut, the metal comprising the lattice, discussed in detail above, is processed to have an $A_F$ less than 15 degrees centigrade. Lowering the $A_F$ without substantially compromising any cold working incorporated into the raw material increases the radial strength. Finally, the number of diamonds comprising the structure is reduced to about eight from eleven or fourteen. In addition, the stent layout has been modified to avoid the overlap between the apexes of the diamonds 114 and the anchoring barbs 120 as illustrated in detail in FIG. 3. Other alloys may be utilized to achieve similar results without resorting to altering the $A_F$. For example, other nickel rich alloys and tertiary NiTi alloys may inherently comprise high plateau stress levels.

Figure 4:
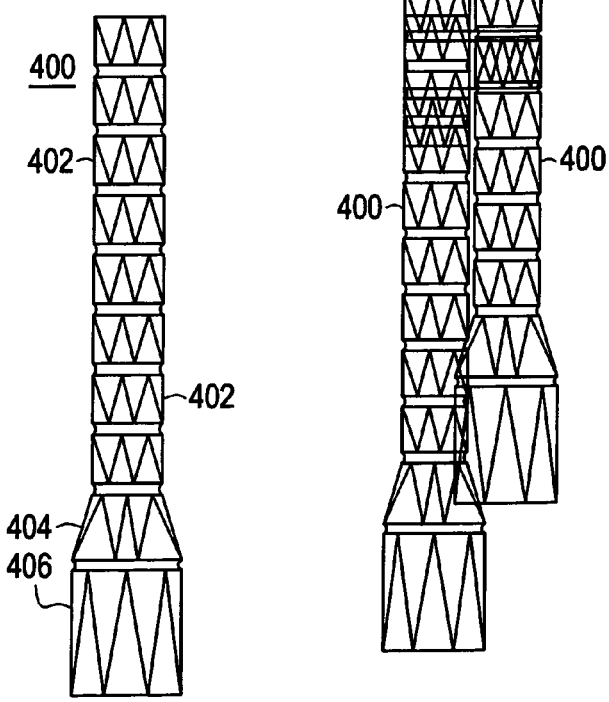
FIG. 4 is a diagrammatic representation of a stent graft in accordance with the present invention.

FIG. 4 illustrates an endoleg or graft that is utilized to bypass the aneurysmal section of the artery. The leg 400 comprises a plurality of individual stent segments 402, a tapered stent segment 404 and an anchoring stent segment 406. The stent segments are secured together by the graft material. The anchoring stent segment 406 is larger than the other stent segments 402 so that the leg 400 may be securely anchored downstream of the aneurysm. The larger diameter requires the use of the tapered stent segment. Each segment comprises a substantially zigzag shaped pattern.

Figure 5:
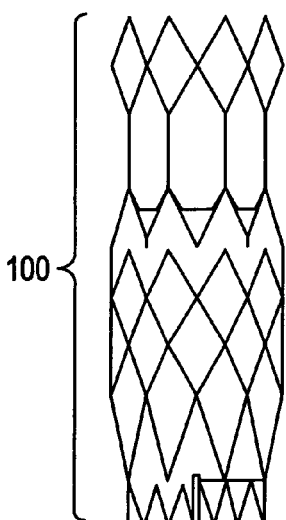
FIG. 5 is a diagrammatic representation of an exemplary abdominal aortic aneurysm repair assembly in accordance with the present invention.

FIG. 5 illustrates the entire system comprising the anchoring and sealing component 100 and two legs 400. Utilizing two legs reduces profiles and allows for the legs to extend into the iliac arteries at the aortic bifurcation.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An endoprosthesis comprising: an anchoring and sealing component having a cranial section comprising a tubular stent defining a longitudinal axis, the stent having an expansion ratio of greater than about 7 and less than about 14, wherein said expansion ratio is achieved by selection of a processing variable selected from the group consisting of the number of apexes or diamonds of the structure, the starting tube dimension, the final austenite temperature and a combination of two or more of aforementioned processing variables, a caudal section having at least two legs in fluid communication with the cranial section, each of the at least two legs comprising a plurality of individual stents, in a staggered arrangement with respect to one another and graft material affixed to at least a portion of the cranial section forming a single flow channel and the at least two legs thereby forming at least two fluid flow conduits in the caudal section, the at least two legs being attached to the cranial section at a bifurcation point and wherein one of the at least two legs is longer than the other by one stent, the at least two legs being attached to one another along the length of the legs up to the bifurcation point such that column strength is increased and wherein one leg comprises an individual stent that is affixed to the graft material, and wherein the stent of the leg and the stent of the cranial section are configured to be in abutting relation when the endoprosthesis is fully extended relative to the longitudinal axis and the other leg does not have a stent in abutting relation to the stent of the cranial section when the endoprosthesis is fully extended relative to the longitudinal axis; and at least two endolegs connectable to the at least two fluid flow conduits of the anchoring and sealing component.

2. The endoprosthesis of claim 1, wherein the stent of the cranial section is comprised of a single row of diamond elements at a first end thereof and multiple rows of diamond elements toward a second end thereof such that the number of diamond elements in the single row or the multiple rows at least partially determines an expansion range and a radial strength of the endoprosthesis.

3. The endoprosthesis of claim 2, whereby the stent of the cranial section is fabricated from a respective tubing such that altering the starting dimensions of the respective tubing optimizes the expansion range and radial strength of the endoprosthesis.

4. The endoprosthesis of claim 3, wherein the stent of the cranial section and the individual stents of the caudal section are comprised of materials from a group consisting of metals, polymers, ceramics and shape memory alloys.

5. The endoprosthesis of claim 4, wherein the materials comprising the stent of the cranial section and the individual stents of the caudal section provide a martensite to austentite transformation at low temperatures.

6. The endoprosthesis of claim 5, wherein altering a final austenite termperature $A_F$ of the respective tubes from which the stent of the cranial section and the individual stent of the caudal section are fabricated maximizes the expansion ratio and radial strength of the endoprosthesis.

\* \* \* \* \*